United States Patent [19]

Nelson et al.

[11] Patent Number: 4,687,800

[45] Date of Patent: Aug. 18, 1987

[54] TARTRATE-BASED LIGHT STABILIZERS FOR PLASTICS

[75] Inventors: Richard V. Nelson, Wilmington, Del.; John F. Stephen, West Chester, Pa.

[73] Assignee: ICI Americas Inc., Wilmington, Del.

[21] Appl. No.: 902,797

[22] Filed: Sep. 2, 1986

Related U.S. Application Data

[63] Continuation of Ser. No. 786,799, Oct. 11, 1985, abandoned.

[51] Int. Cl.[4] .................. C07D 405/12; C07D 405/14; C08K 5/34

[52] U.S. Cl. ....................... 524/103; 524/98; 524/102; 546/19; 546/187; 540/596

[58] Field of Search .................. 546/19, 187; 524/102, 524/103, 98; 540/596

[56] References Cited

U.S. PATENT DOCUMENTS 4,608,436 8/1986 Cantatore et al. .................. 546/187

*Primary Examiner*—Robert T. Bond
*Attorney, Agent, or Firm*—Richard A. Rowe

[57] ABSTRACT

Tartrate-derived acetal esters and amides possessing the polyalkyl piperidin-4-yl moiety are useful light stabilizers with synthetic polymer resins such as polyolefins and, in particular, polypropylene.

15 Claims, No Drawings

TARTRATE-BASED LIGHT STABILIZERS FOR PLASTICS

This is a continuation, of co-pending application Ser. No. 06/786,799 filed on Oct. 11, 1985, now abandoned.

The invention is directed to polymeric compositions which are resistant to degradation when exposed to actinic radiation. In particular, it is directed to resins such as polypropylene stabilized with effective amounts of cyclic acetals of aldehydes and ketones containing the polyalkylpiperidine moiety. The invention is further directed to a novel group of substances which are useful as additives for synthetic polymers which act to retard photodegradation.

Many synthetic organic polymers deteriorate rapidly when exposed to sunlight. To circumvent this rapid degradation many additives have been developed to stabilize these resins against the harmful radiation. These additives include hydroxybenzophenones, hydroxybenzotriazoles, organonickel complexes, and a number of compounds which incorporate a hindered amine, such as 2,2,6,6-tetraalkylpiperidine, that is substituted in the 4-position. However, because none of these compounds sufficiently satisfy the stabilization requirements of polymers in their wide variety of forms and applications, there remains a need for new substances which will be more fully satisfactory.

The polymer compositions of the invention are made by the incorporation of an effective amount of a cyclic acetal of formula I with the resin to be stabilized. These acetals may be selected from those having the structures of formula I as shown in the Table of Structures which follows wherein:

$R^1$ is selected from hydrogen and an alkyl group of 1-5 carbon atoms such as methyl, ethyl, n-propyl, n-butyl, n-pentyl, especially hydrogen and methyl and most preferably hydrogen;

$R^2$ is selected from hydrogen, oxyl, hydroxyl, a straight or branched chain methylene-linked alkyl group having from 1 up to 18 carbon atoms such as methyl, ethyl, octyl, octadecyl, or 2-ethylhexyl, an alkanoyl group having 2-18 carbon atoms, such as acetyl, propanoyl, butanoyl, isopentanoyl, or stearoyl, an alkenyl group of 3-4 carbon atoms, an alkenoyl group having 3-6 carbon atoms, such as acryloyl, methacryloyl, crotonyl, an alkynyl group having 3 to 6 carbon atoms such as propargyl, or 2-butynyl, a cyanomethyl group, a 2,3-epoxypropyl group, an unsubstituted or substituted benzyl group of 7 to 15 carbon atoms such as 3,5-di-tert-butyl-4-hydroxybenzyl, 3-tert-butyl-4-hydroxybenzyl or 3-tert-butyl-4-hydroxy-5-methylbenzyl, a group —$CH_2CH(OR^5)$—$R^6$ and a group of the formula

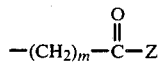

wherein Z is a group selected from —$OR^7$ and —$N(R^8)(R^9)$ when m is 1 or 0 and when m is 0, Z can be a group —$C(O)$—$OR^{10}$.

$R^5$ is selected from hydrogen, an aliphatic group of 1-18 carbon atoms such as those of $R^2$, an araliphatic group such as benzyl and phenethyl, and an aliphatic acyl group having 2-18 carbon atoms such as those of $R^2$, $R^6$ is selected from hydrogen, an alkyl group of 1-16 carbon atoms and phenyl, $R^7$ is selected from an alkyl group of 1-18 carbon atoms, a cycloalkyl of 5-12 carbon atoms such as cyclopentyl, cyclohexyl, cyclooctyl, cyclododecyl, allyl, benzyl, phenyl, and a group of formula II wherein $R^1$ and $R^2$ are as described above, and $R^8$ and $R^9$, same or different, are selected from hydrogen, an alkyl group having 1-8 carbon atoms such as methyl, ethyl, hexyl, a cycloalkyl group having 5-12 carbon atoms such as those of $R^7$, an aryl group having 6-10 carbon atoms such as 4-methylphenyl, 2-methylphenyl, 4-butylphenyl, and aralkyl groups having 7-15 carbon atoms such as benzyl, o,m,p-alkylsubstituted benzyl, and phenethyl. In addition, $R^8$ and $R^9$ together with the nitrogen atom to which they are attached can form a 5-7 membered ring such as pyrrolidine, piperidine and homopiperidine, and $R^{10}$ is selected from $C_{1-18}$ alkyl such as those of $R^2$, phenyl or benzyl, and is preferably $C_{1-2}$ alkyl.

$R^3$ and $R^4$ may independently be selected from hydrogen, an alkyl group of 1 to 14 carbon atoms such as methyl, ethyl, n-propyl, isopropyl, isooctyl, 3-heptyl, an alkenyl group of 2 to 4 carbon atoms, aryl, aralkyl, a group —$(CH_2)_nCO$—$OR^{11}$ where n is 0 or 1, and a group of formula III. $R^{11}$ is selected from a straight or branched chain alkyl group of up to 18 carbon atoms in length or a group of formula II.

When $R^3$ is hydrogen $R^4$ can be a group of formula IV where A is a 1 to 4 carbon alkylene group, a phenylene group or a direct bond.

When $R^3$ is methyl $R^4$ can be a group of formula V where p is 1 or 2.

$R^3$ and $R^4$ together with the carbon atoms to which they are attached can form a cycloalkyl group having 5-12 carbon atoms such as cyclopentyl, cyclohexyl, cyclooctyl, cyclododecyl or denote a group of the formula VI or the group of formula VII where the carbon atom labelled 2 is the same as that labelled 2 in formula I.

X is either —O— or —$NR^{12}$— where $R^{12}$ is selected from hydrogen or an alkyl group of 1-8 carbon atoms such as methyl, ethyl, butyl, or octyl.

The acetals of formula I can be prepared from the corresponding aldehyde or ketone by reacting them with a diol of the formula [$R^{13}O_2C$-$CH(OH)$-$]_2$ using a suitable acid catalyst and a suitable solvent as generally known in the art for the preparation of acetals. Examples of suitable acid catalysts are numerous, however, without introducing any limitations are mentioned p-toluenesulfonic acid and methanesulfonic acid. Examples of suitable solvents are cyclohexane and benzene. Although $R^{13}$ may be any alkyl group of 1 to 18 carbon atoms for this reaction it is preferred that $R^{13}$ be ethyl or methyl. These diols are known commonly as diethyl and dimethyl tartrate, respectively, and are commercially available.

Several of the acetals serving as precursors to the compounds of this invention have been reported previously. In particular these compounds may be found in the works of Y. Tsuzuki, Bull. Chem. Soc. Jap. 11, 362 (1936), 12, 487 (1937), and 14, 35 (1939), K. Satsumabayashi, et al., Nippon Shika Daigaku Kiyo 1978, 7, 147-164, and J. Wolinski, et al., Acta Pol. Pharm. 41 (4), 425-8 (1984).

These acetals are then transformed into the corresponding piperidine compounds of the invention in either a single step or in the cases where $R^2$ is other than hydrogen or alkyl an additional step is generally use. The transesterification or amidation reaction can be performed either neat or in a suitable solvent using basic catalysis as commonly used in the art. Examples of suitable catalysts without introducing any limitations are lithium amide and sodium methoxide. Examples of suitable solvents are ligroine and toluene.

The 4-hydroxypolyalkylpiperidines and the 4-aminopolyalkylpiperidines used to convert the acetals into the compounds of the invention are know from German Pat. No. 2,352,658 and U.S. Pat. No. 3,684,765. In general, the 4-hydroxy compounds are prepared from the corresponding 4-oxopiperidines by reduction via catalytic hydrogenation over Raney Nickel and the 4-amino compounds are synthesized via a reductive amination using ammonia or the particular primary amine of interest.

The 4-oxopiperidines of formula VIII can be prepared by reaction of ammonia with an aliphatic ketone. The reaction of ammonia with acetone to yield triacetonamine is well-known and various processes exist in the art for its manufacture. The reaction of ammonia with methyl ethyl ketone has been described by W. Traube in Chem. Ber. 41,777 (1908).

Compounds of the formula VIII which carry other alkyl substituents in the 2-position and the 6-position can be prepared in a two step process following the procedures outlined in Helv. Chim. Act 30,1114 (1947) and Monatsh. Chem. 88,464 (1957), followed by hydrolysis of the resulting pyrimidine.

The introduction of any alkyl, alkenyl, alkynyl, aralkyl and 2,3-epoxypropyl group can be achieved by reaction of the initially prepared ester or amide containing the free N-H of the polysubstituted piperidine with suitable halides like methyl iodide, ethyl bromide, propyl bromide, dodecyl chloride, and octadecyl chloride: allyl bromide, methallyl chloride, butenyl chloride, propargyl bromide, benzyl chloride, phenethyl bromide, and epichlorohydrin. The generated hydrogen halide can be scavenged by the addition of an inorganic base such as carbonate of hydroxide or by the addition of an organic amine such a triethylamine to the reaction mixture.

An alternative way of preparing the compounds of the invention which contain a 1-alkyl, 1-alkenyl, 1-alkynyl, 1-aralkyl, or 2,3-epoxypropyl group, especially when the desired invention compound is an ester, is to prepare the 1-substituted polyalkylpiperidin-4-ol as described in U.S. Pat. No. 4,014,887 and perform the transesterification in the manner as stated previously.

The introduction of an alkanoyl or an alkenoyl group can be performed by acylation of the parent N-H compound using the suitable acid halide or, when convenient, the acid anhydride. If the acid halide is used the generated hydrogen halide can be scavenged in the same manner as stated previously. Examples of such groups are acetyl chloride, propionyl chloride, hexanoyl chloride, dodecanoyl chloride, octacdecanoyl chloride, acetic anhydride, and propionic anhydride.

For the compounds when $R^2$ is the group $-CH_2CH(OR^5)-R^6$ the substituent can be introduced by reaction of the parent N—H compound with the corresponding alkylene oxide such as ethylene oxide, propylene oxide and styrene oxide. The resulting hydroxy compound can be acylated in the manner commonly known in the art using the suitable acid halide and can be alkylated by generating the alkoxide using a base like sodium hydride and treating it with the desired alkyl or aralkyl halide.

When $R^2$ is the group $-CH_2-_m$ and m is zero the appropriate group can be attached by reacting the parent N-H compound with a chloroformate such as methyl chloroformate, ethyl chloroformate, allyl chloroformate, hexylchloroformate, decyl chloroformate, octadecyl chloroformate, and phenyl chloroformate. The preparation of the oxamide half esters can be achieved by reaction of the parent N-H compound with the oxalyl chloride monoalkylester such as oxalyl chloride monomethylester and oxalyl chloride monoethylester and scavenging the generated hydrogen chloride with a base as stated previously.

For preparation of the corresponding ureas the parent N-H compound can be treated with the suitable carbamyl halide such as methyl carbamyl chloride, ethyl carbamyl chloride, butyl carbamyl chloride, penyl carbamyl chloride, dimethyl carbamyl chloride, diethylcarbamyl chloride, dihexylcarbamyl chloride, pyrrolidinyl carbamyl chloride, piperidine carbamyl chloride, and homopiperidine carbamyl chloride. Alternatively, the ureas can be prepared by treating the parent N—H compound with suitable isocyanate.

Compounds of formula I wherein $R^2$ is the oxyl radical are obtainable from the corresponding N—H compounds by oxidation with a peroxide such as hydrogen peroxide in the presence of a catalyst like sodium tungstate or with percarboxylic acids like metachloroperoxybenzoic acid.

When $R^2$ is the group $-(CH_2)_m-COZ$ and m is 1 the appropriate group can be attached by reacting the parent N—H compound with an ester of chloroacetic acid such as methyl chloroacetate, ethyl chloroacetate, cyclohexychloroacetate, benzyl chloroacetate, allyl chloroacetate and phenyl chloroacetate.

The compounds of this invention are effective light stabilizers for synthetic organic polymers.

The following examples are offered to demonstrated but not limit the scope of the invention.

EXAMPLE 1

1,4-Dioxaspiro[4.5]decane-2,3-dicarboxylic acid, diester with 2,2,6,6-tetramethylpiperidin-4-ol Preparation A -
1,4-Dioxaspiro[4.5]decane-2,3-dicarboxylic acid, diethylester To a mixture of diethyl tartrate (14.40 g, 69.8 mmol) and cyclohexanone (6.86 g, 69.8 mmol) in 50 ml of cyclohexane was added paratoluenesulfonic acid (0.5 g, 2.6 mmol) as catalyst. The mixture was heated to reflux and the generated water was removed via a Dean-Stark trap. Upon completion of the ketalization (about 4 hours) the mixture was cooled to ambient temperature, washed with dilute aqueous sodium hydroxide and then with water. After drying over sodium sulfate and concentrating under reduced pressure a yellow liquid was obtained (14.75 g, 74%). Distillation under vacuum yielded the desired substance as a colorless liquid, b.p. 131°-132° C. at 0.5-1.0 mm.

A mixture of the compound of Preparation A (11.26 g, 39.3 mmol) and 2,2,6,6-tetramethylpiperidin-4-ol (12.37 g, 39.3 mmol) in 50 ml of ligroine (90°-110° C.) was heated to reflux under a gentle stream of nitrogen. Lithium amide (80 mg) was added as catalyst. The distillate was collected in a Dean-Stark trap and drained intermittently in the first hour. After 21 hours at reflux the reaction mixture was removed from the heat, diluted with ligroine, the catalyst was neutralized with glacial acetic acid, and the mixture was filtered. Concentration yielded a pale yellow solid (13.46 g, 67%). Recrystallization from ligroine yielded the desired substance as a white crystalline solid, mp 111.5°–113° C.

Analysis Calculated for:
$C_{28}H_{48}N_2O_6$: C, 66.11%; H, 9.51%; N, 5.51%.
Found: C, 66.00%; H, 9.12%; N, 5.93%.

EXAMPLE 2

2[1-Ethylpentyl]-1,3-dioxolane-4,5-dicarboxylic acid, diester with 2,2,6,6-tetramethylpiperidin-4-ol Preparation B - 2[1-Ethylpentyl]-1,3-dioxolane 4,5-dicarboxylic acid, diethyl ester To a mixture of diethyl tartrate (13.03 g, 63.2 mmol) and 2-ethylhexanal (8.10 g, 63.2 mmol) in 40 ml of cyclohexane was added methanesulfonic acid (0.3 g) as catalyst. The reaction mixture was heated to reflux and the generated water was removed by using a Dean-Stark trap. After 6–7 hours the reaction was essentially complete. After cooling to ambient temperature the mixture was washed with dilute aqueous sodium hydroxide and then with water. Drying and concentration yielded a yellow liquid (16.8 g, 84%). Distillation yielded the desired product as a colorless liquid, b.p. 128°–133° C. at 08 mm.

The product of Preparation B (5.87 g, 18.5 mmol) and 2,2,6,6-tetramethylpiperidin-4-ol (6.29 g, 40.0 mmol) were combined in 50 ml of ligroine and heated to reflux under a gentle stream of nitrogen. Lithium amide (46 mg) was added as catalyst and the ligroine was removed from the Dean-Stark trap intermittently during the first hour. After 7 hours the reaction mixture was allowed to cool, diluted with 25 ml of ligroine and the catalyst was neutralized with glacial acetic acid. The mixture was partitioned with water, dried and concentrated via rotary evaporator. The light yellow residue (9.3 g) was a viscous liquid which was confirmed spectroscopically to be the desired compound.

Analysis Calculated for:
$C_{30}H_{54}N_2O_6$: C, 66.88%; H, 10.10%; N, 5.20%.
Found: C, 66.17%; H, 9.86%; N, 5.01%.

EXAMPLE 3

2-[1-Ethylpentyl]-1,3-dioxolane-4,5-dicarboxylic acid, diester with 1,2,2,6,6-pentamethylpiperidin-4-ol To a mixture of the compound of Preparation B (3.35 g, 10.6 mmol) and 1,2,2,6,6-pentamethylpiperidin-4-ol (3.80, 22.2 mmol) in 60 ml of ligroine at reflux under a gentle stream of nitrogen was added the lithium amide (25 mg) as catalyst. The distillate was collected in a Dean-Stark trap which was drained intermittently during the initial hour of reaction. After 3 hours at reflux the mixture was cooled, diluted with ligroine (25 ml) and the catalyst was neutralized with glacial acetic acid. The mixture was partitioned with water, dried over sodium sulfate and concentrated via rotary evaporator to yield a colorless viscous liquid (5.87 g, 97%).

Analysis Calculated for:
$C_{32}H_{58}N_2O_6$: C, 67.81%; H, 10.31%; N, 4.94%.
Found: C, 67.48%; H, 10.33%; N, 4.66%.

EXAMPLE 4

2-[1-Methylethyl]-1,3-dioxolane-4,5-dicarboxylic acid, diester with 2,2,6,6-tetramethylpiperidin-4-ol Preparation C—2-[1-Methylethyl]-1,3-dioxalane -4,5-dicarboxylic acid, diethyl ester Diethyl tartrate was reacted with isobutyraldehyde according to the procedure outlined for Preparation A.

To a mixture of the material of Preparation C (10.78 g, 41 mmol) and 2,2,6,6-tetramethylpiperidin4-ol (13.02 g, 82 mmol) in 120 ml of ligroine (90°–110° C.) at reflux and under a gentle stream of nitrogen, was added lithium amide (48 mg). The solution was heated for about 3–4 hours at which point additional ligroine (60 ml) was added along with glacial acetic acid to neutralize the catalyst. The mixture was filtered and concentrated to yield a viscous light yellow liquid. Purification yielded the desired material (18.1 g, 91%) as confirmed by spectroscopic methods.

Analysis Calculated for:
$C_{26}H_{46}N_2O_6$: C., 64.70%; H, 9.61%; N, 5.80%.
Found: C, 64.31%; H, 9.69%; N, 5.51%.

EXAMPLE 5

Butyric acid, 3-[1,3-dioxolane-4,5-dicarboxylic acid], mixture of di- and triesters with 2,2,6,6-tetramethylpiperidin-4-ol Preparation D - Butyric acid, 3-[1,3-dioxolane-4,5-dicarboxylic acid]triethyl ester Diethyl tartrate was reacted with ethyl acetoacetate according to the procedure outlined for Preparation A. The desired substance was obtained as a colorless liquid, b.p. 139°–140° C. at 0.8 mm.

To a mixture of the compound of Preparation D (2.44 g, 7.6 mmol) and 2,2,6,6-tetramethylpiperidin4-ol (3.62 g, 23 mmol) in 35 ml of ligroine at reflux and under a gentle stream of nitrogen was added lithium amide (20 mg) as catalyst. The reaction was allowed to proceed for 20 hours before cooling, neutralizing the catalyst with acetic acid and filtering the precipitated unreacted alcohol. The filtrate was concentrated to yield a viscous, light yellow liquid (4.3 g) which was composed of the di- (major) and tripiperidinol esters as shown spectroscopically.

EXAMPLE 6

2-[1-Methylethyl]-1,3-dioxolane-4,5-dicarboxylic acid, diester with 1-acetyl-2,2.6,6-tetramethyl piperidin-4-ol A mixture of the compound of Example 4 (29.39g, 61 mmol), and acetic anhydide (49.82 g, 488 mmol) was refluxed for 21 hours. The acetic anhydride was removed by distillation and the yellow residue was dissolved in 150 ml of chloroform. The solution was neutralized with 10% aqueous NaOH, washed with water (3×100 ml) and then dried over sodium sulfate and concentrated to leave a yellow oil. Trituration with ether and petroleum ether (35°–60° C.) yielded a white solid. Recyrstallization from 5:1 hexane/ethyl acetate yielded 19.05 g (55% yield) of the product as a white powder, mp 95°–96° C.

Analysis Calculated for:
$C_{30}H_{50}N_2O_8$: C, 63.58%; H, 8.89%; N, 4.94%.
Found: C, 63.17%; H, 8.95%; N, 4.98%.

EXAMPLE 7

1,4-dioxaspiro[4.5]decane-2,3-dicarboxylic acid, diester with 1-acetyl-2,2,6,6-tetramethylpiperidin-4-ol A mixture of the compound of Example 1 (20.30 g, 40 mmol) and acetic anhydride (32.59 g, 320 mmol) was refluxed for 32 hours. The acetic anhydride was then removed by distillation and the yellow-brown residue was dissolved in 100 ml of chloroform. After adding 10% NaOH to neutralize the solution the organic phase was washed with water (3×100 ml), dried ($Na_2SO_4$) and concentrated to yield a yellow oil. Trituration with ether and petroleum ether (35°–60° C.) yielded a white solid (20.29 g, 85%) having a melting point of 107°–108° C. The product was characterized by NMR and mass spectroscopy.

EXAMPLE 8

2-[1-Ethylpentyl]-1,3-dioxolane-4,5-dicarboxylic acid, diester with 1-acetyl-2,2,6,6-tetramethyl piperidin-4-ol A mixture of the compound of Example 2 (22.74 g, 42 mmol) and acetic anhydride (34.31 g, 336 mmol) was refluxed for five hours whereupon the acetic anhydride was removed by distillation. The yellow residue was dissolved in 100 ml of chloroform, washed with dilute sodium hydroxide and with water (2×100 ml) and then dried over sodium sulfate. Concentration yielded a yellow-orange oil which upon trituration with petroleum ether (35°–60° C.) yielded 11.21 g (42%) of a white powder, mp 80°–81° C. The product was characterized by NMR and mass spectroscopy.

EXAMPLE 9

Butric acid, 3-[1,3-dioxolane-4,5-dicarboxylic acid], mixture of di- and triesters with 1-acetyl-2,2,6,6-tetromethylpiperidin-4-ol A mixture of the compound of Example 5 (10.61 g, 16 mmol) and acetic anhydride (19.6 g, 0.19 mol) was heated at reflux for 48 hours. The acetic anhydride was removed by distillation. The residue was dissolved in 100 ml of chloroform and was washed with dilute sodium hydroxide and water (3×100 ml). The organic solution was dried over sodium sulfate and concentrate to yield a yellow-brown viscous residue weighing 12.0 g. The product was characterized by NMR and mass spectroscopy.

The cyclic acetal derivatives of the invention are particularly useful as light stabilizers for synthetic polymers which undergo degradation in the presence of air and electromagnetic radiation. As used herein polymers are intended to embrace polyolefins including homopolymers of olefins such as low density and high density polyethylene, polypropylene, polystyrene, polybutadiene, polyisoprene and the like and copolymers of olefins with other ethylenically unsaturated monomers such as ethylene-propylene copolymer, ethylene-butylene copolymer, ethylene-vinyl acetate copolymer, styrenebutadiene copolymer, acrylonitrile-styrene-butadiene copolymer and the like; polyvinylchlorides and polyvinylidene chlorides including homopolymers of each of vinyl chloride and vinylidene chloride, vinyl chloridevinylidene copolymers and copolymers of each vinyl chloride and vinylidene chloride with vinyl acetate or other ethylenically unsaturated monomer; poly-acetal such polyoxymethylene and polyoxyethylene; polyesters such as polyethyleneterephthalate; polyamide such as 6-nylon, 6,6-nylon and 6,10-nylon, polyurethanes, and polymers derived from $\alpha,\beta$-unsaturated acids and derivatives thereof, polyacrylates and polymethacrylates, polyacrylic amides and polyacrylonitrile, as well as copolymers of acrylic acid and one or more of its derivatives with a melamine-formaldehyde resin.

Synthetic polymers have been widely utilized in the art in view of their excellent properties in various forms or shapes for example filaments, fibers, yarns, filament sheet, other molded articles and other molded articles made from latex and foam. However, these polymers have some drawbacks such as poor light and heat stabilities among others. Stated illustratively, polyolefins and polyurethane elastomers frequently tend to undergo severe deterioration when exposed to light such as sunlight or ultraviolet light and polyvinyl chloride and polyvinylidene chlorides frequently tend to deteriorate and become colored by the action of light and heat together with elimination of hydrogen chloride. Polyamides are also frequently subjected to photodegradation. For the purpose of stabilizing these synthetic polymers against such that rather have here to for been proposed in the art a number of stabilizers for example in the case of polyolefins, benzotriazole and benzophenone compounds; for polyurethanes, phenol compounds and benzophenone compounds; and for polyvinylchlorides and vinylidene chlorides, lead salts such as basic lead silicate and trisilicate, lead maleate and organic tin compounds such as dibutyltinlaurate and dibutyltinmaleate.

The resin should have incorporated therewith an effective stabilizing amount of formula I compound. The amount will depend upon the nature of the plastic and the amount of radiation to which the plastic will be subject. Generally an amount between about 0.01% and 5.0% by weight of the polymer is effective. Preferably they may be used in concentrations between 0.05 and 1% by weight.

In addition to the light stabilizers of formula I may be used fillers and additional stabilizers including antioxidants, flame retardant stabilizers, anti-slipping and antistatic agents, supplemental light stabilizers, pigments, dyes, lubricants, etc.

Suitable antioxidants include those of the hindered phenol type such as 2,6-di-t-butyl-p-cresol; 4,4'-bis(2,6-di-t-butylphenol); 4,4'-bis(2,6-diisoprophylphenol); 2,4,6-tri-t-butylphenol; 2,2'-thiobis (4-methyl-6-t-butylphenol); octadecyl-2(3',5'-di-t-butyl -4'-hydroxyphenyl)propionate; pentaerythrityl tetrakis(3,5-di-t-butyl-4-hydroxyphenyl)propionate; 1,3,5-tris(3',5'-di-t-butyl-4 -hydroxybenzyl) iso-cyanurate; 1,3,5-tris((3',5'-di-t-butyl-4'-hydroxyphenyl) propionate) isocyanurate; 1,3,5-tris-(3',5'-di-t-butyl-4'-hydroxybenzyl)-2,4,6-dimethylbenzyl) -s-triazine-2,4,6-(1H,3H,5H)-trione and esters of thiodipropionic acid such as dilaurylthiodipropionate and distearothiodipropionate etc.; hydrocarbyl phosphites such as triphenyl phosphite, trinonyl phosphite, didodecyl pentaerythrityl diphosphite, diphenyldecyl phosphite, tris-(2,4-di-t-butylphenyl)-phosphite, bis(2,4-di-t-butylphenyl)pentaerythrityl diphosphite, etc, in combinations thereof.

Suitable supplemental light stabilizers include those of the benzotriazole class, such as 2-(2'-hydroxy-5-t-octylphenyl)benzotriazole; 2,(2'-hydroxy -3',5'-di-t-butyl-phenyl)-5-chlorobenzotriazole; 2-(2'-hydroxy-5'-methylphenyl)benzotriazole; 2-(2'-hydroxy-3'-t-butyl-5'-methylphenyl)-5-chlorobenzotriazole; 2-(2'-hydroxy- 5'-t-butylphenyl)benzotriazole; 2-(2'-hydroxy-3',5'-di-t-amylphenyl)benzotriazole; those of the hydroxybenzophenone type such as 2-hydroxy-4-methoxybenzophenone; 2-hydroxy-4-octyloxybenzophenone; 2,2'-dihydroxy-4,4'-dimethoxybenzophenone; hindered phenol esters, such as n-hexadecyl-3,5-di-t-butyl-4-hydroxybenzoate, and 2',4'-di-t-butylphenol-3,5-di-t-butyl-4-hydroxybenzoate; metal complexes such as nickel complexes of 2,2'-thiobis(4-6-octylphenol), nickel butylamine complexes of 2,2'-thiobis(4-t-octylphenol); nickel complexes of bis(4-t-octyl-phenol)sulphone; nickel dibutyl thiocarbamate; nickel salts of 4-hydroxy-3,5-di-t-butylbenzylphosphonic acid monoalkyl esters where alkyl is methyl, ethyl, propyl, butyl etc.; nickel complexes of to 2-hydroxy-4-methylphenyl undecylketoneoxime. Further illustrative examples of suitable antioxidants of supplemental light stabilizers can be found in columns 3 and 4 of U.S. Pat. Nos. 3,488,290 and 3,496,134.

EXAMPLE 10-14

In order to illustrate the effectiveness of the above-described compounds as light stabilizers the previously described materials of Examples 1-5 were each incorporated into a commercially available polypropylene resin manufactured by Hercules Corporation as PROFAX TM 6301 Polypropylene Resin. The light stabilizers may be incorporated with the polypropylene by solvent blending (methylene chloride) at concentrations of 0.25% by weight of the total resin composition and as a primary antioxidant, stearyl β-3,5-di-t-butyl -4-hydroxyphenylpropionate is used at a concentration of 0.2%. The resin is then extruded at 200° C. and compression molded at 6,000 psi at 188° C. to produce films having thicknesses of 5 mils. Each test film and control film is exposed to Xenon Arc in an Atlas weather-o-meter until the infrared carbonyl adsorption increased by 0.5, which is considered to be the failure point.

| Example No. | Stabilizer | Hours to Failure |
|---|---|---|
|  | Control | 490 |
| 10 | Product of Example 1 | 3710 |
| 11 | Product of Example 2 | 3110 |
| 12 | Product of Example 3 | 3525 |
| 13 | Product of Example 4 | 3080 |
| 14 | Product of Example 5 | >1750 |

TABLE OF STRUCTURES

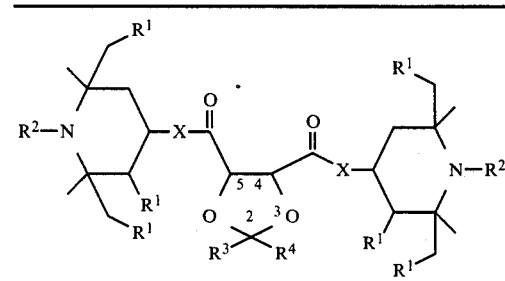
(I)

TABLE OF STRUCTURES -continued

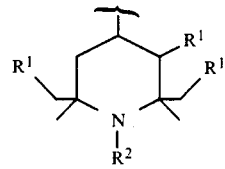
(II)

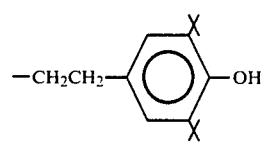
(III)

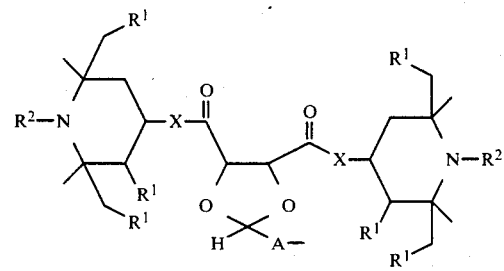
(IV)

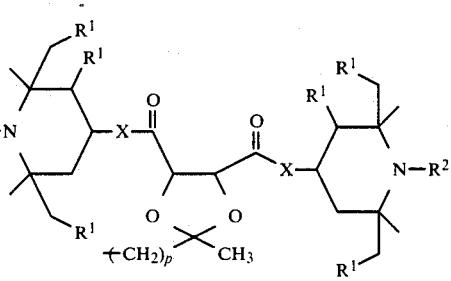
(V)

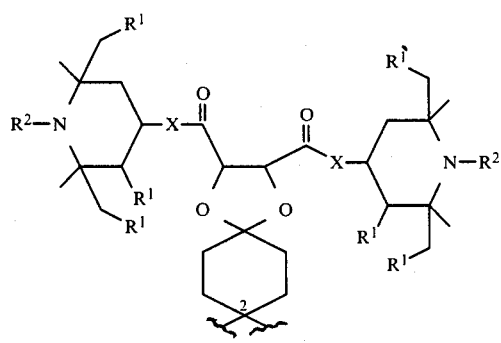
(VI)

-continued
TABLE OF STRUCTURES

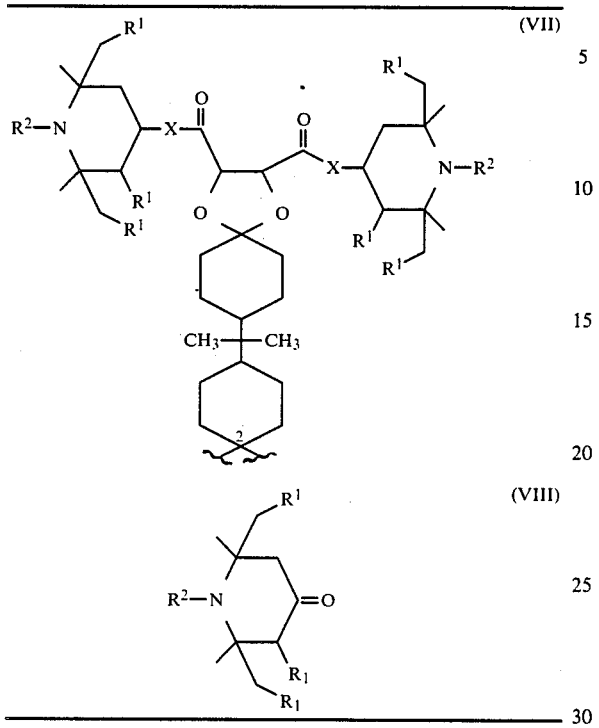

(VII)

(VIII)

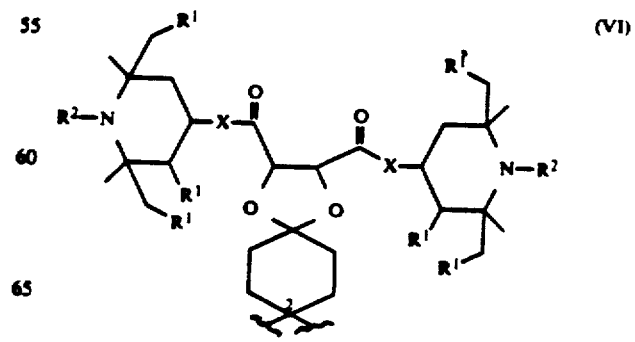

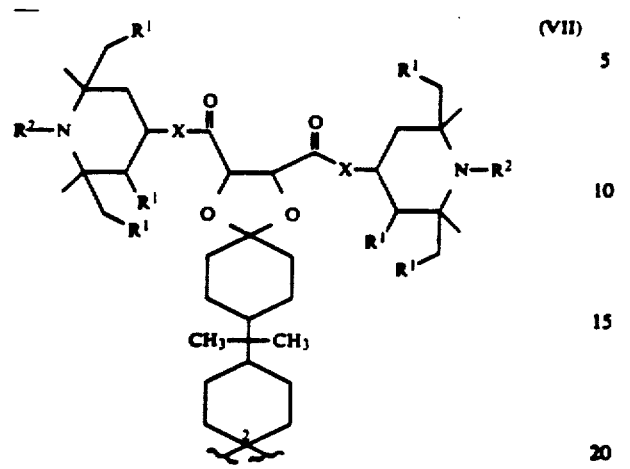

What is claimed is:

1. A compound of the formula I wherein $R^1$ is selected from hydrogen and an alkyl group of 1-5 carbon atoms, $R^2$ is selected from hydrogen, oxyl, hydroxyl, a straight or branched chain methylene linked alkyl group having from 1 to 18 carbon atoms, an alkanoyl group having 2-18 carbon atoms, an alkenoyl group having 3 to 6 carbon atoms, an alkynyl group having 3 to 6 carbon atoms, a cyanomethyl group, a 2,3-epoxypropyl group, a benzyl or an alkyl substituted benzyl group having 7-15 carbon atoms, a group—$CH_2CH(OR^5)$—$R^6$ and a group of the formula

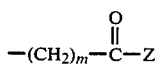

wherein Z is a group selected from —$OR^7$ and —$N(R^8)(R^9)$ when m is 1 or 0 and when m is 0, Z can be a group —CO—$OR^{10}$, wherein $R^5$ is selected from hydrogen, an aliphatic group of 1-18 carbon atoms, an araliphatic group, and an aliphatic acyl group having 2-18 carbon atoms described for said $R^2$, $R^6$ is selected from hydrogen, an alkyl group of 1 to 16 carbon atoms and phenyl, $R^7$ is selected from an alkyl group from 1 to 18 carbon atoms, a cycloalkyl group of 5-12 carbon atoms, and a group of formula II, $R^8$ and $R^9$, same or different, are selected from hydrogen, an alkyl group having 1-18 carbon atoms, a cycloalkyl group having 5-12 carbon atoms, an aryl group having 6-10 carbon atoms and aralkyl groups having 7-15 carbon atoms, $R^8$ and $R^9$ together with the nitrogen atom to which they are attached can form a pyrrolidine, piperidine or homopiperidine ring, $R^{10}$ is selected from an aliphatic group of 1-18 carbon atoms, phenyl and benzyl, $R^3$ and $R^4$ may independently be selected from hydrogen or an alkyl group of 1-14 carbon atoms, an alkenyl group of 2-4 carbon atoms, a group —$(CH_2)_nCO$—$OR$ 11 where n is 0 or 1, and a group of formula III, wherein $R^{11}$ is selected from an alkyl group having up to 18 carbon atoms or a group of formula II, when $R^3$ is hydrogen $R^4$ is a group of formula IV where A is a 1-4 carbon alkylene group, a phenylene group or a direct bond, when $R^3$ is methyl $R^4$ can be a group of formula V where p is 1 or 2, $R^3$ together with the carbon atoms to which they are attached can form a cycloalkyl group having 5-12 atoms or denote a group of the formula VI or the group of formula VII wherein the C atom labelled 2 is the same as that labelled 2 in formula I, X is either —O or —$NR^{12}$—where $R^{12}$ is selected from hydrogen or an alkyl group of 1-8 carbon atoms, and wherein said formulas are:

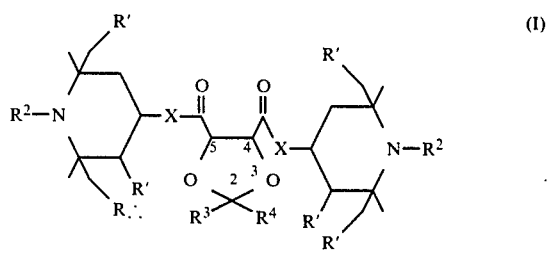

(I)

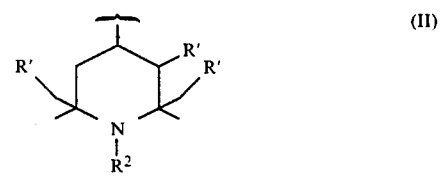

(II)

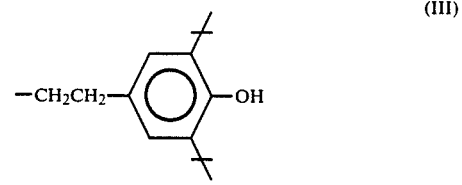

(III)

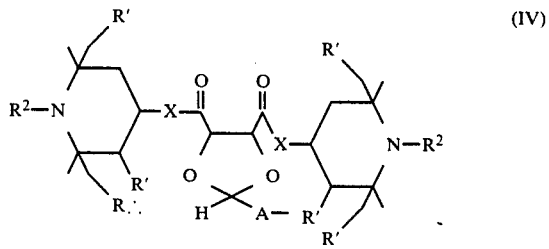

(IV)

-continued

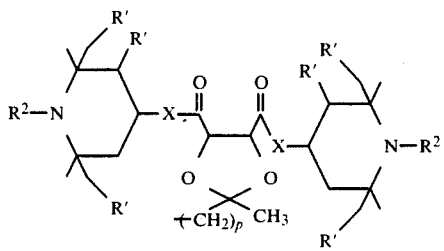
(V)

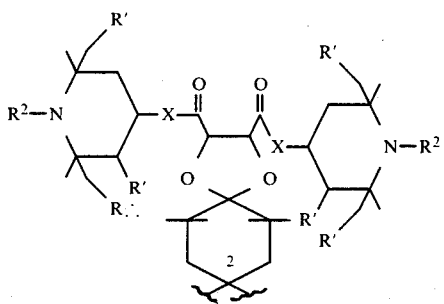
(VI)

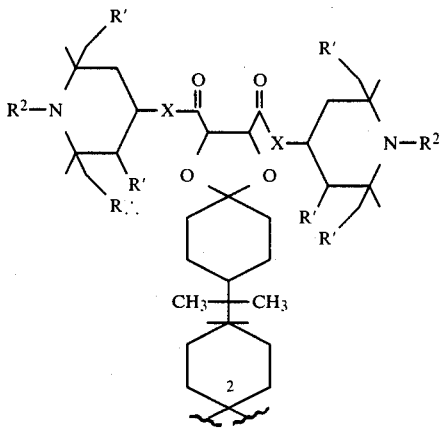
(VII)

2. A compound of claim 1 wherein $R^1$ is hydrogen, and X is —O—.

3. A compound of claim 2 which is 1,4-dioxaspiro-[4.5]decane-2,3-dicarboxylic acid, diester with 2,2,6,6-tetramethylpiperidin-4-ol.

4. A compound of claim 2 which is 2-[1-ethylpentyl]-1,3-dioxolane-4,5-dicarboxylic acid, diester with 2,2,6,6-tetramethylpiperidin-4-ol.

5. A compound of claim 2 which is 2-[1-ethylpentyl]-1,3-dioxolane-4,5-dicarboxylic acid, diester with 1,2,2,6,6-pentamethylpiperidin-4-ol.

6. A compound of claim 2 which is 2-[1-methylethyl]-1,3-dioxolane-4,5-dicarboxylic acid, diester with 2,2,6,6-tetramethylpiperidin-4-ol.

7. A compound of claim 2 which is butyric acid, 3-[1,3-dioxolane-4,5-dicarboxylic acid], mixture of di- and triesters with 2,2,6,6-tetramethylpiperidin-4-ol.

8. A compound of claim 2 which is 2-[1-methylethyl]-1,3-dioxolane-4,5-dicarboxylic acid, diester with 1-acetyl-2,2,6,6-tetramethylpiperidin-4-ol.

9. A compound of claim 2 which is 1,4-dioxaspiro[4.5]-decane-2,3-dicarboxylic acid, diester with 1-acetyl-2,2,6,6-tetramethylpiperidin-4-ol.

10. A compound of claim 2 which is 2-[1-ethylpentyl]-1,3-dicarboxylic acid, diester with 1-acetyl-2,2,6,6-tetramethylpiperidin-4ol.

11. A compound of claim 2 which is butyric acid, 3-[1,3-dioxolane-4,5-dicarboxylic acid], mixture of di- and triesters with 1-acetyl-2,2,6,6-tetremethylpiperidin-4-ol.

12. A synthetic polymer composition stabilized against light induced deterioration comprising an organic polymer normally subject to deterioration by light, and from 0.01–5% by weight of a compound of claim 1.

13. A composition of claim 12 wherein the organic polymer is a polyolefin homopolymer or copolymer.

14. A composition of claim 13 wherein said polyolefin is polypropylene.

15. A method of stabilizing organic polymers against light induced deterioration which comprises incorporating therewith from 0.01–5% by weight of a compound of claim 1.

* * * * *

UNITED STATES PATENT AND TRADEMARK OFFICE
CERTIFICATE OF CORRECTION

PATENT NO. : 4,687,800

DATED : August 18, 1987

INVENTOR(S) : Richard V. Nelson et al

It is certified that error appears in the above-identified patent and that said Letters Patent is hereby corrected as shown below:

The structures in Formulas VI and VII in Claim 1, Columns 12 and 13, should appear as they do in Columns 10 and 11. (as per attached sheet)

Signed and Sealed this

Eighth Day of March, 1988

Attest:

DONALD J. QUIGG

*Attesting Officer*    *Commissioner of Patents and Trademarks*

UNITED STATES PATENT AND TRADEMARK OFFICE
CERTIFICATE OF CORRECTION

PATENT NO. : 4,687,800

DATED : August 18, 1987

INVENTOR(S) : Richard V. Nelson et al

It is certified that error appears in the above-identified patent and that said Letters Patent is hereby corrected as shown below: